United States Patent
Mito

(10) Patent No.: US 6,376,427 B1
(45) Date of Patent: Apr. 23, 2002

(54) HERBICIDAL COMPOSITIONS

(75) Inventor: Nobuaki Mito, Kobe (JP)

(73) Assignee: Sumitomo Chemical Company, Limited, Osaka (JP)

( * ) Notice: Subject to any disclaimer, the term of this patent is extended or adjusted under 35 U.S.C. 154(b) by 0 days.

(21) Appl. No.: 09/807,940

(22) PCT Filed: Oct. 18, 1999

(86) PCT No.: PCT/JP99/05738

§ 371 Date: Apr. 20, 2001

§ 102(e) Date: Apr. 20, 2001

(87) PCT Pub. No.: WO00/24257

PCT Pub. Date: May 4, 2000

(30) Foreign Application Priority Data

Oct. 23, 1998 (JP) .......................................... H10-302736

(51) Int. Cl.[7] ........................ A01N 43/58; A01N 43/824
(52) U.S. Cl. ....................................................... 504/137
(58) Field of Search ........................................ 504/137

(56) References Cited

U.S. PATENT DOCUMENTS 5,858,920 A    1/1999   Dahmen et al. ............ 504/103
6,090,753 A    7/2000   Katayama et al. .......... 504/238
6,121,194 A    9/2000   Mito ............................ 504/134

FOREIGN PATENT DOCUMENTS

| DE | 19546751 | | 6/1996 |
| EP | 0 860 435 | A1 | 8/1998 |
| JP | 10-231213 | | 9/1998 |
| WO | 98/.35556 | | 8/1998 |

OTHER PUBLICATIONS

European Search Report dated Oct. 1, 2001.

*Primary Examiner*—S. Mark Clardy
(74) *Attorney, Agent, or Firm*—Sughrue Mion, PLLC

(57) ABSTRACT

The present invention relates to a herbicidal composition containing 2-chloro-4-fluoro-5-(4-methyl-5-trifluoromethyl-3-pyridazinon-2-yl)phenoxyacetic acid ester and 4-fluoro-N-isopropyl-2-(5-trifluoromethyl-1,3,4-thiadiazol-2-yloxy)-acetanilide (flufenacet or fluthiamide) as active ingredients, and a method for controlling weeds comprising applying them to soil or weeds.

A variety of weeds in many places can be controlled, especially a variety of weeds in wheat field, barley field, oat field, rye field, soybean field, corn field or the like can be controlled selectively without causing phytotoxicity to wheat, barley, oat, rye, soybean, corn by the present invention.

8 Claims, No Drawings

HERBICIDAL COMPOSITIONS

This application is a 371 of PCT JP99/05738 filed Oct. 10, 1999.

TECHNICAL FIELD

The present invention relates to a herbicidal composition, especially, a herbicidal composition suitable for controlling weeds in fields of wheat, barley, oat, rye, soybean, corn, and a method for controlling weeds utilizing the herbicidal composition.

BACKGROUND ART

At the present time, numerous herbicides are commercially available and used. There are, however, many species of weeds to be controlled and their growth extends over a long time. For this reason, requested are herbicides with higher herbicidal activity, wider herbicidal spectrum, and no problems for phytotoxicity to crops.

DISCLOSURE OF INVENTION

The present inventor has intensively studied to find out excellent herbicides. As a result, he has found that various weeds growing in crop lands or non-crop lands can be effectively controlled by applying a herbicidal composition containing as active ingredients, 2-chloro-4-fluoro-5-(4-methyl-5-trifluoromethyl-3-pyridazinon-2-yl)phenoxyacetic acid ester and 4-fluoro-N-isopropyl-2-(5-trifluoromethyl-,1, 3,4-thiadiazol-2-yloxy)acetanilide (common name; flufenacet, hereinafter, referred to as flufenacet) to soil or weeds. He has further found that the herbicidal activity is synergistically increased as compared with the cases where the active ingredients are independently used, and the herbicidal composition can, therefore, be applied at a lower amount; and that the herbicidal spectrum is expanded and especially, a wide variety of weeds can be controlled in fields of wheat, barley, oat, rye, soybean and corn, thereby completing the present invention.

Thus, the present invention provides a herbicidal composition comprising as active ingredients, 2-chloro-4-fluoro-5-(4-methyl-5-trifluoromethyl-3-pyridazinon-2-yl) phenoxyacetic acid ester and flufenacet (hereinafter referred to as the present composition) and a method for controlling weeds which comprises applying them to soil or weeds.

The ester of the 2-chloro-4-fluoro-5-(4-methyl-5-trifluoromethyl-3-pyridazinon-2-yl)phenoxyacetic acid ester which is one active ingredient of the present composition represents C1–C7 alkylester, C5–C6 cycloalkylester, C2–C6 alkenylester and the like. The 2-chloro-4-fluoro-5-(4-methyl-5-trifluoromethyl-3-pyridazinon-2-yl)phenoxyacetic acid ester can be produced according to the method described in WO 97/07104 or the similar methods. Examples of the ester are shown in the following Table 1.

TABLE 1

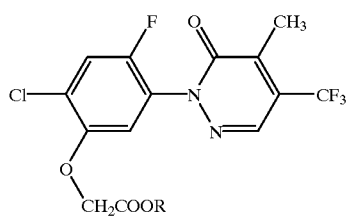

| Compound Symbol | R |
|---|---|
| A | Ethyl |
| B | Methyl |
| C | Propyl |
| D | Butyl |
| E | Pentyl |
| F | Hexyl |
| G | Heptyl |
| H | i-Propyl |
| I | i-Butyl |
| J | t-Butyl |
| K | c-Pentyl |
| L | c-Hexyl |
| M | Allyl |
| N | Vinyl |

("i-", "t-", and "c-" represent iso-, tertiary-, and cyclo-, respectively.)

Flufenacet is a compound described in AG CHEM NEW COMPOUND REVIEW, VOLUME 16, 1998 (AG CHEM INFORMATION SERVICES), at 11 page.

The present composition has a herbicidal activity to a wide variety of weeds. Examples of the weeds are shown below.

Polygonaceous weeds:
wild buckwheat (*Polygonum convolvulus*), pale smartweed (*Polygonum lapathifolium*), pennsylvania smartweed (*Polygonum pensylvanicum*), ladysthumb (*Polygonum persicaria*), curly dock (*Rumex crispus*), broadleaf dock (*Rumex obtusifolius*) Japanese knotweed (*Polygonum cuspidatum*)

Portulacaceous weeds:
common purslane (*Portulaca oleracea*)

Caryophyllaceous weeds:
common chickweed (*Stellaria media*)

Chenopodiaceous weeds:
common lambsquarters (*Chenopodium album*), kochia (*Kochia scoparia*)

Amaranthaceous weeds:
redroot pigweed (*Amaranthus retroflexus*), smooth pigweed (*Amaranthus hybridus*)

Cruciferous (brassicaceous) weeds:
wild radish (*Raphanus raphanistrum*), wild mustard (*Sinapis arvensis*), shepherdpurse (*Capsella bursa-pastoris*)

Leguminous (fabaceous) weeds:
hemp sesbania (*Sesbania exaltata*), sicklepod (*Cassia obtusifolia*), Florida beggarweed (*Desmodium tortuosum*), white clover (*Trifolium repens*)

Malvaceous weeds:
velvetleaf (*Abutilon theophrasti*), prickly sida (*Sida spinosa*)

Violaceous weeds:
field pansy (*Viola arvensis*), wild pansy (*Viola tricolor*)

Rubiaceous weeds:
catchweed bedstraw (cleavers) (*Galium aparine*)

Convolvulaceous weeds:
  ivyleaf morningglory (*Ipomoea hederacea*), tall morningglory (*Ipomoea purpurea*), entireleaf morningglory (*Ipomoea hederacea var. integriuscula*), pitted morningglory (*Ipomoea lacunosa*), field bindweed (*Convolvulus arvensis*)
Labiate weeds:
  red deadnettle (*Lamium purpureum*), henbit (*Lamium amplexicaule*)
Solanaceous weeds:
  jimsonweed (*Datura stramonium*), black nightshade (*Solanum nigrum*)
Scrophulariaceous weeds:
  birdseye speedwell (*Veronica persica*), ivyleaf speedwell (*Veronica hederaefolia*)
Composite weeds:
  common cocklebur (*Xanthium pensylvanicum*), common sunflower (*Helianthus annuus*), scentless chamomile (*Matricaria perforata orinodora*), cornmarigold (*Chrysanthemum segetum*), pineappleweed (*Matricaria matricarioides*), common ragweed (*Ambrosia artemisiifolia*), giant ragweed (*Ambrosia trifida*), horseweed (*Erigeron canadensis*), Japanese mugwort (*Artemisia princeps*), tall goldenrod (*Solidago altissima*)
Boraginaceous weeds:
  forget-me-not (*Myosotis arvensis*)
Asclepiadaceous weeds:
  common milkweed (*Asclepias syriaca*)
Euphorbiaceous weeds:
  sun spurge (*Euphorbia helioscopia*), spotted spurge (*Euphorbia maculata*)
Graminaceous weeds:
  barnyardgrass (*Echinochloa crus-galli*), green foxtail (*Setaria viridis*), giant foxtail (*Setaria faberi*), large crabgrass (*Digitaria sanguinalis*), goosegrass (*Eleusine indica*), annual bluegrass (*Poa annua*), blackgrass (*Alopecurus myosuroides*), wild oat (*Avena fatua*), johnsongrass (*Sorghum halepense*), quackgrass (*Agropyron repens*), downy brome (*Bromus tectorum*), bermudagrass (*Cynodondactylon*), fall panicum (*Panicum dichotomiflorum*), Texas panicum (*Panicum texanum*), shattercane (*Sorghum vulgare*)
Commelinaceous weeds:
  common dayflower (*Commelina communis*)
Equisetaceous weeds:
  field horsetail (*Equisetum arvense*)
Cyperaceous weeds:
  rice flatsedge (Cyperusiria), purplenutsedge (*Cyperus rotundus*), yellow nutsedge (*Cyperus esculentus*)

On the other hand, the present composition exhibits no significant phytotoxicity on "mugi" (wheat, barley, rye, oat, etc.), corn, soybean and the like as crops.

The present composition exhibits selectivity between weeds and crops such as mugi, corn and soybean. Accordingly, the present composition is suitable for controlling weeds in fields of mugi, corn, soybean by being used in said fields. The fields of mugi in the present invention represent the field of wheat (*Triticum aestivum*), barley (*Hordeum vulgare*), rye (Secale cereale), oat (*Avena sativa*) and the like.

The present composition can be used in agricultural/horticultural field such as agricultural field in which till cultivation and no-till cultivation are conducted, and orchard; non-agricultural field such as play ground, vacant lot, wood railroad side.

In the present composition, the mixing ratio of 2-chloro-4-fluoro-5-(4-methyl-5-trifluoromethyl-3-pyri-dazinon-2-yl)phenoxyacetic acid ester and flufenacet as active ingredients, although it may vary with the species of weeds to be controlled, situation and conditions of application and the like, is usually 1:1 to 100, preferably 1:2 to 50 by weight.

The present composition may be usually used in the form of formulations such as emulsifiable concentrates, wettable powders, flowables, granules and the like which can be prepared by mixing with solid carriers, liquid carriers, and the like, and if necessary, adding surfactants, other adjuvants and the like. In such a formulation, 2-chloro-4-fluoro-5-(4-methyl-5-trifluoromethyl-3-pyridazinon-2-yl)phenoxyacetic acid ester and flufenacet are usually contained at the total amount of 0.5 to 90% by weight, preferably 1 to 80% by weight.

The solid carrier to be used in the formulation may include, for example, the following materials in fine powder or granule form: clays (e.g., kaolinite, diatomaceous earth, synthetic hydratedsiliconoxide, Fubasami clay, bentonite, acid clay); talc and other inorganic minerals (e.g., sericite, powdered quartz, powdered sulfur, activated carbon, calcium carbonate); and chemical fertilizers (e.g., ammonium sulfate, ammoniumphosphate, ammonium nitrate, ammonium chloride, urea). The liquid carrier may include, for example, water; alcohols (e.g., methanol, ethanol); ketones (e.g., acetone, methyl ethyl ketone, cyclohexanone); aromatic hydrocarbons (e.g., toluene, xylene, ethylbenzene, methylnaphthalene); non-aromatic hydrocarbons (e.g., hexane, cyclohexane, kerosine); esters (e.g., ethyl acetate, butyl acetate); nitriles (e.g., acetonitrile, isobutyronitrile); ethers (e.g., dioxane, diisopropyl ether); acid amides (e.g., dimethylformamide, dimethylacetamide); and halogenated hydrocarbons (e.g., dichloroethane, trichloro- ethylene).

The surfactant may include, for example, alkylsulfric acid esters; alkylsulfonic acid salts; alkylarylsulfonic acid salts; alkyl aryl ethers and their polyoxyethylene derivatives; polyethylene glycol ethers; polyhydric alcohol esters; and sugar alcohol derivatives.

The other adjuvants may include, for example, adhesive agents and dispersing agents, such as casein, gelatin, polysaccharides (e.g., starch, gumarabic, cellulose derivatives, alginic acid), lignin derivatives, bentonite, and synthetic water-soluble polymers (e.g., polyvinyl alcohol, polyvinyl pyrrolidone, polyacrylic acid); and stabilizers such as PAP (isopropyl acid phosphate), BHT (2,6-di-tert-butyl-4- methylphenol), BHA (2-/3-tert-butyl-4-methyoxyphenol), vegetableoils, mineral oils, fatty acids, and fatty acid esters.

The present composition can also be prepared by making each active ingredient into the above formulation and then mixing these formulations.

The present composition thus formulated may be applied as such, or after diluted with water or the like. Further, the present composition may also be used in admixture with other herbicides, in which case the herbicidal activity can be expected to be enhanced. The present composition can also be used together with insecticides, bactericides, fungicides, plant growth regulators, fertilizers, safener, soil conditioners, or the like.

The application amount of the present composition, although it may vary with the mixing ratio of 2-chloro-4-fluoro-5- (4-methyl-5-trifluoromethyl-3-pyridazinon-2-yl)-phenoxyacetic acid ester and flufenacet as the active ingredient compounds, weather conditions, formulation types, application times, application methods, application places, weeds to be controlled, and crops to be protected, is usually 10 to 2000 g, preferably 20 to 1000 g as the total amount of active ingredient compounds per hectare. In the case of emulsifiable concentrates, wettable powders, flowables, or the like, they are usually applied after diluted in their prescribed amounts with water at a ratio of 100to 1000 liters per hectare. Also, in case of foliar treatment of the present composition to weeds, the dilution of the present composition with water in which the adjuvant is added may be expected to enhance the effect against weeds.

The following will describe formulation examples, in which parts are by weight.

FORMULATION EXAMPLE 1

Four parts of compound A, B, C, D, E, F, G, H, I, J, K, L, M or N, 40 parts of flufenacet, 3 parts of calcium lignin sulfonate, 2 parts of sodium laurylsulfate, and 51 parts of synthetic hydrated silicon oxide are well pulverized and mixed to give a wettable powder.

FORMULATION EXAMPLE 2

Fourteen parts of compound A, B, C, D, E, F, G, H, I, J, K, L, M or N, 70 parts of flufenacet, 3 parts of calcium lignin sulfonate, 2 parts of sodium laurylsulfate, and 11 parts of synthetic hydrated silicon oxide are well pulverized and mixed to give a wettable powder.

FORMULATION EXAMPLE 3

Five parts of compound A, B, C, D, E, F, G, H, I, J, K, L, N or N, 10 parts of flufenacet, 3 parts of calcium lignin sulfonate, 2 parts of sodium laurylsulfate, and 80 parts of synthetic hydrated silicon oxide are well pulverized and mixed to give a wettable powder.

FORMULATION EXAMPLE 4

One part of compound A, B, C, D, E, F, G, H, I, J, K, L, M or N, 50 parts of flufenacet, 3 parts of calcium lignin sulfonate, 2 parts of sodium laurylsulfate, and 44 parts of synthetic hydrated silicon oxide are well pulverized and mixed to give a wettable powder.

FORMULATION EXAMPLE 5

Three parts of compound A, B, C, D, E, F, G, H, I, J, K, L, M, or N, 30 parts of flufenacet, 3 parts of polyoxyethylene sorbitan monooleate, 3 parts of CMC (carboxymethylcellulose), and 61 pares of water are mixed and wet pulverized until the particle size comes to 5 microns or smaller to give a flowable.

FORMULATION EXAMPLE 6

One parts of compound A, B, C, D, E, F, G, H, I, J, K, L, M or N, 50 parts of flufenacet, 3 parts of polyoxyethylene sorbitan monooleate, 3 parts of CMC (carboxymethylcellulose), and 43 parts of water are mixed and wet pulverized until the particle size comes to 5 microns or smaller to give a flowable.

FORMULATION EXAMPLE 7

Three parts of compound A, B, C, D, E, F, G, H, I, J, K, L, M or N, 6 parts of flufenacet, 3 parts of polyoxyethylene sorbitan monooleate, 3 parts of CMC (carboxymethylcellulose), and 85 parts of water are mixed and wet pulverized until the particle size comes to 5 microns or smaller to give a flowable.

FORMULATION EXAMPLE 8

0.5 Part of compound A, B, C, D, E, F, G, H, I, J, K, L, M or N, 25 parts of flufenacet, 3 parts of polyoxyethylene sorbitan monooleate, 3parts of CMC (carboxymethylcellulose), and68.5parts of water are mixed and wet pulverized until the particle size comes to 5 microns or smaller to give a flowable.

The following will describe test examples.

Evaluation Criteria

The herbicidal activity is evaluated at 11 levels with indices of 0 to 10, i.e., shown by numeral "0", "1", "2", "3", "4", "5", "6", "7", "8", "9", or "10", wherein "0" means that there was no or little difference in the degree of germination or growth between the treated plants and the untreated plants at the time of examination, and "10" means that the test plants died completely or their germination or growth was completely inhibited.

TEST EXAMPLE 1

Plastic pots each having an area of $26.5 \times 19 cm^2$ and a depth of 10 cm were filled with upland soil, and then seeded with wheat and giant foxtail. The wheat was grown for 14 days and t he giant foxtail was grown for 23 days in a greenhouse.

An emulsifiable concentrate compound A which had been obtained by well mixing 10 parts of compound A, 14 parts of polyoxyethylene styryl phenyl ether, 6 parts of calcium dodecylbenzenesulfonate, 35 parts of xylene, and 35 parts of cyclohexanone, an emulsifiable concentrate of flufenacet which had been obtained by well mixing 10 parts of flufenacet, 14 parts of polyoxyethylene styryl phenyl ether, 6 parts of calcium dodecylbenzenesulfonate, 35 parts of xylene, and 35 parts of cyclohexanone, and a mixture of the emulsifiable concentrate of compound A and the emulsifiable concentrate of flufenacet were independently diluted in their prescribed amounts with water. Each dilution was uniformly sprayed over the plants with a small sprayer. After the application, the plants were grown in the greenhouse for 5 days, and the herbicidal activity and safety to wheat were then examined. The results are shown in Table 2.

TABLE 2

| Test Compound | Dosage (g/ha) | Herbicidal activity Giant foxtail | Phytotoxicity Wheat |
| --- | --- | --- | --- |
| Compound A | 10 | 3 | No harm |
| Flufenacet | 240 | 2 | No harm |
| Compound A + Flufenacet | 10 + 240 | 8 | No harm |

TEST EXAMPLE 2

Plastic pots each having an area of $26.5 \times 19\ cm^2$ and a depth of 7 cm were filled with upland soil, and then seeded with soybean, corn and giant foxtail. The corn was grown for 13 days, and the soybean and giant foxtail were grown for 22 days in a greenhouse. An emulsifiable concentrate compound A which had been obtained by well mixing 10 parts of compound A, 14 parts of polyoxyethylene styryl phenyl ether, 6 parts of calcium dodecylbenzenesulfonate, 35 parts of xylene, and 35 parts of cyclohexanone, an emulsifiable concentrate of flufenacet which had been obtained by well mixing 10 parts of flufenacet, 14 parts of polyoxyethylene styryl phenyl ether, 6 parts of calcium dodecylbenzenesulfonate, 35 parts of xylene, and 35 parts of cyclohexanone, and a mixture of the emulsifiable concentrate of compound A and the emulsifiable concentrate of flufenacet were independently diluted in their prescribed amounts with water. Each dilution was uniformly sprayed over the plants with a small sprayer. After the application, the plants were grown in the greenhouse for 5 days, and the herbicidal activity and safety to soybean and corn were then examined. The results are shown in Table 3.

TABLE 3

| Test Compound | Dosage (g/ha) | Herbicidal activity Giant foxtail | Phytotoxicity Soybean | Corn |
|---|---|---|---|---|
| Compound A | 40 | 4 | No harm | No harm |
| Flufenacet | 400 | 2 | No harm | No harm |
| Compound A + Flufenacet | 40 + 400 | 9 | No harm | No harm |

By using the present composition, a wide variety of weeds, especially a variety of weeds in fields of wheat, barley, oat, rye, soybean, corn and the like, can be controlled selectively without causing phytoeoxicity to wheat, barley, oat, rye, soybean and corn.

What is claimed is:

1. A herbicidal composition containing as active ingredients, 2-chloro-4-fluoro-5-(4-methyl-5-trifluoromethyl-3-pyridazinon-2-yl)phenoxyacetic acid ester and 4-fluoro-N-isopropyl-2-(5-trifluoromethyl-1,3,4-thiadiazol-2-yloxy)acetanilide.

2. The herbicidal composition according to claim 1, wherein the weight ratio of 2-chloro-4-fluoro-5-(4-methyl-5-trifluoromethyl-3-pyridazinon-2-yl)phenoxyacetic acid ester and 4-fluoro-N-isopropyl-2-(5-trifluoromethyl-1,3,4-thiadiazol-2-yloxy)acetanilide is in the range of 1:1 to 1:100.

3. A method for controlling weeds, which comprises applying 2-chloro-4-fluoro-5-(4-methyl-5-trifluoromethyl-3-pyridazinon-2-yl)phenoxyacetic acid ester and 4-fluoro-N-isopropyl-2-(5-trifluoromethyl-1,3,4-thiadiazol-2-yloxy)acetanilide to places in which weeds grow or will grow.

4. The method for controlling weeds according to claim 3, wherein the place is wheat field, barley field, oat field, rye field, soybean field or corn field.

5. A method for controlling weeds, which comprises applying 2-chloro-4-fluoro-5-(4-methyl-5-trifluoromethyl-3-pyridazinon-2-yl)phenoxyacetic acid ester and 4-fluoro-N-isopropyl-2-(5-trifluoromethyl-1,3,4-thiadiazol-2-yloxy)acetanilide to weeds in wheat field, barley field, oat field, or rye field.

6. A method for controlling weeds, which comprises applying 2-chloro-4-fluoro-5-(4-methyl-5-trifluoromethyl-3-pyridazinon-2-yl)phenoxyacetic acid ester and 4-fluoro-N-isopropyl-2-(5-trifluoromethyl-1,3,4-thiadiazol-2-yloxy)acetanilide to weeds in soybean field.

7. A method for controlling weeds, which comprises applying 2-chloro-4-fluoro-5-(4-methyl-5-trifluoromethyl-3-pyridazinon-2-yl)phenoxyacetic acid ester and 4-fluoro-N-isopropyl-2-(5-trifluoromethyl-1,3,4-thiadiazol-2-yloxy)acetanilide to weeds in corn field.

8. The method for controlling weeds according to claim 3, 4, 5, 6 or 7, which comprises applying 2-chloro-4-fluoro-5-(4-methyl-5-trifluoromethyl-3-pyridazinon-2-yl)phenoxyacetic acid ester and 4-fluoro-N-isopropyl-2-(5-trifluoromethyl-1,3,4-thiadiazol-2-yloxy) acetanilide in a total amount of 10 to 2000 g per hectare.

* * * * *